US012620410B2

(12) United States Patent
Duke et al.

(10) Patent No.: US 12,620,410 B2
(45) Date of Patent: May 5, 2026

(54) ALIGNING PARAMETER DATA WITH AUDIO RECORDINGS

(71) Applicant: Stryker Corporation, Kalamazoo, MI (US)

(72) Inventors: Steven Barry Duke, Bothell, WA (US); Fred W. Chapman, Newcastle, WA (US)

(73) Assignee: Stryker Corporation, Portage, MI (US)

( * ) Notice: Subject to any disclaimer, the term of this patent is extended or adjusted under 35 U.S.C. 154(b) by 727 days.

(21) Appl. No.: 17/865,788

(22) Filed: Jul. 15, 2022

(65) Prior Publication Data

US 2023/0019463 A1 Jan. 19, 2023

Related U.S. Application Data

(60) Provisional application No. 63/222,937, filed on Jul. 16, 2021.

(51) Int. Cl.
| | |
|---|---|
| *G10L 25/87* | (2013.01) |
| *A61N 1/39* | (2006.01) |
| *G10L 15/26* | (2006.01) |
| *G10L 21/055* | (2013.01) |
| *G16H 10/60* | (2018.01) |

(52) U.S. Cl.
CPC ............... *G10L 25/87* (2013.01); *A61N 1/39* (2013.01); *A61N 1/3937* (2013.01); *G10L 15/26* (2013.01); *G10L 21/055* (2013.01); *G16H 10/60* (2018.01)

(58) Field of Classification Search
CPC ....... G10L 25/87; G10L 15/26; G10L 21/055; G10L 25/48; G16H 15/00
See application file for complete search history.

(56) References Cited

U.S. PATENT DOCUMENTS

| | | | | |
|---|---|---|---|---|
| 5,549,115 | A * | 8/1996 | Morgan ................. | G01D 9/005 600/508 |
| 5,683,423 | A * | 11/1997 | Post ..................... | A61N 1/3925 600/522 |
| 6,041,257 | A * | 3/2000 | MacDuff ............... | G01D 9/005 607/5 |
| 7,245,964 | B2 | 7/2007 | Moore et al. | |
| 2004/0172070 | A1 * | 9/2004 | Moore ................... | G16H 10/20 607/5 |

(Continued)

*Primary Examiner* — Pierre Louis Desir
*Assistant Examiner* — Keisha Y. Castillo-Torres
(74) *Attorney, Agent, or Firm* — Lee & Hayes, P.C.

(57) ABSTRACT

Various techniques relate to aligning parameters and audio recordings obtained at a rescue scene. An example method includes receiving, from a first device, a first file including first measurements of a first parameter at first discrete times in a time interval. The first file further indicates a marker output by the first device during the time interval. The method also includes receiving, from a second device, a second file comprising second measurements of a second parameter at second discrete times in the time interval. The method includes detecting the marker output by the first device in the second measurements of the second parameter and based on detecting the signal output by the first device in the second measurements, generating aligned data by time-aligning the first measurements of the first parameter and the second measurements of the second parameter. The method further includes outputting the aligned data.

20 Claims, 8 Drawing Sheets

(56)　　　　　　References Cited

U.S. PATENT DOCUMENTS

| | | | |
|---|---|---|---|
| 2008/0255465 A1* | 10/2008 | Nelson ................... | A61B 5/339 |
| | | | 600/523 |
| 2019/0329057 A1* | 10/2019 | Teber ................... | A61N 1/3968 |
| 2021/0322265 A1* | 10/2021 | Helkowski ........... | A61H 31/005 |

* cited by examiner

RECEIVE, FROM A MEDICAL DEVICE, PARAMETER DATA
702

RECEIVE, FROM A RECORDER, AN AUDIO RECORDING
704

GENERATE ALIGNED DATA BY TIME-ALIGNING THE PARAMETER DATA
AND THE AUDIO RECORDING
706

ALIGNING PARAMETER DATA WITH AUDIO RECORDINGS

CROSS-REFERENCE TO RELATED APPLICATION

This application claims the benefit of U.S. Provisional Application No. 63/222,937, which was filed on Jul. 16, 2021 and is incorporated by reference herein in its entirety.

BACKGROUND

Many emergency service providers use recorders to document emergency scenes. For example, an emergency medical service (EMS) responder carries and activates an independent audio recorder when they respond to an emergency event. The obtained audio recording can be used for post-event review and documentation. However, in some cases, it is difficult to identify the time interval documented in the audio recording. With organizations that have multiple responders and multiple recordings, it can be difficult to identify which audio recordings correspond to which emergency events.

DETAILED DESCRIPTION

Figure 1:
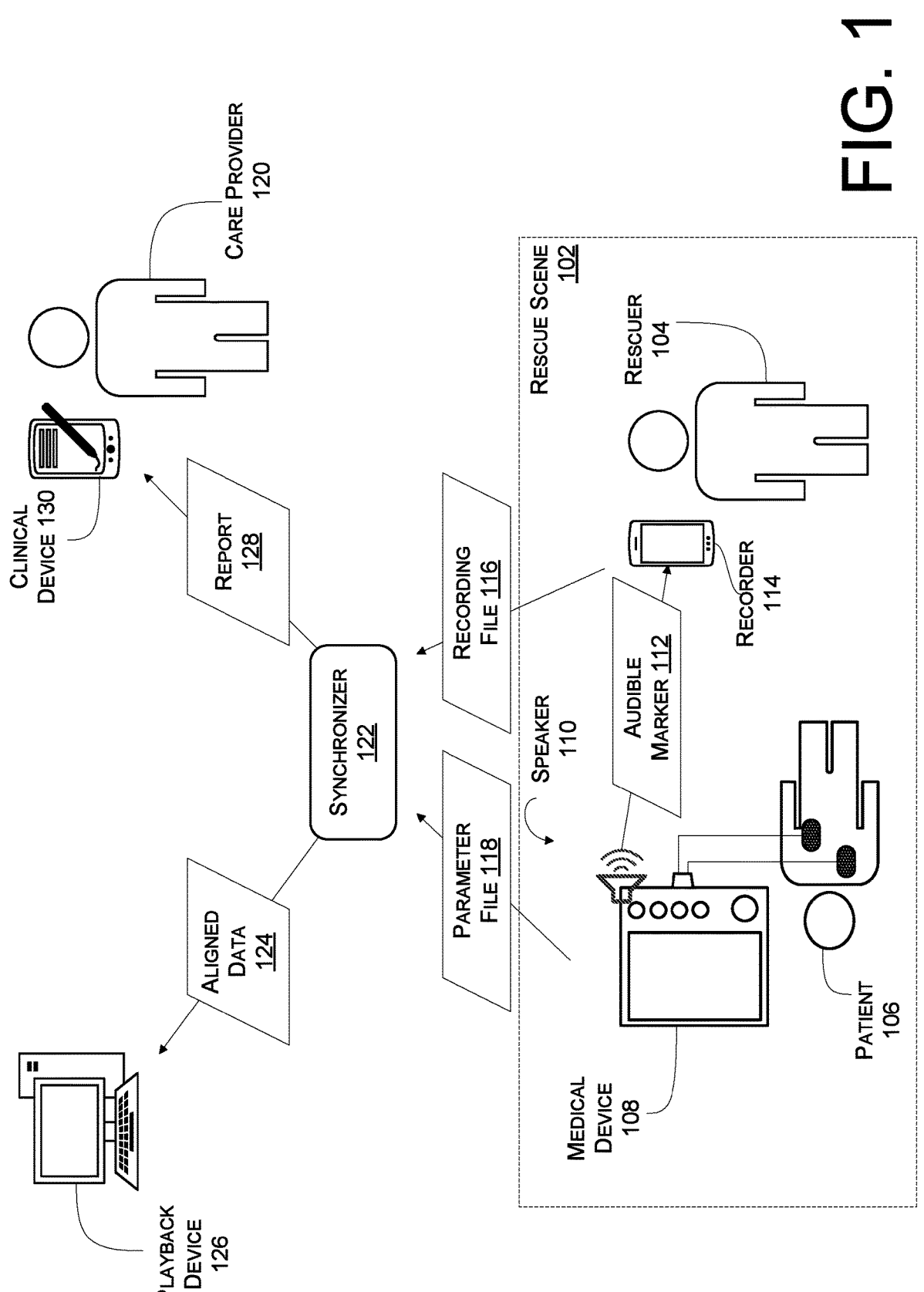
FIG. 1 illustrates an example environment for synchronizing different types of captured data.

FIG. 1 illustrates an example environment 100 for synchronizing different types of captured data. As shown, the environment 100 includes a rescue scene 102 in which a rescuer 104 is treating a patient 106. The rescue scene 102, in some implementations, is a geographic area, volume, or other physical environment. In some examples, the rescue scene 102 is outside of a formal, clinical environment (e.g., a hospital). For example, the rescue scene 102 is outdoors, in a school, in an airport, or some other non-clinical building. The rescuer 104 is an individual caring for the patient 106. Examples of the rescuer 104 include a bystander, an emergency medical service provider or another type of care provider, such as a nurse, physician, or physician's assistant. The patient 106 is an individual being cared for by the rescuer 104. In various implementations, the patient 106 is experiencing acute distress and/or a medical emergency. In some examples, the patient 106 is experiencing cardiac arrest.

The rescuer 104 uses a medical device 108 to diagnose the patient 106, treat the patient 106, or both. In some examples, the medical device 108 is a defibrillator, such as a monitor-defibrillator or an automated external defibrillator (AED). In some cases, the medical device 108 is an ultrasound device configured to generate an ultrasound image of the patient 106 and/or to detect a blood pressure of the patient 106. In some examples, the medical device 108 is a ventilation device configured to provide assisted ventilation to the patient 106. The medical device 108, in various implementations, includes one or more sensors configured to detect a physiological parameter of the patient 106. As used herein, the term "physiological parameter," and its equivalents, may refer to a vital sign or other metric indicative of a condition of an individual. For instance, the medical device 108 includes a detection circuit electrically coupled to electrodes that are disposed on the chest of the patient 106, wherein the detection circuit is configured to detect a transthoracic impedance of the patient 106, an electrocardiogram (ECG) of the patient 106, or a combination thereof. Other examples of physiological parameters include an oxygenation of the patient's 106 blood (e.g., a peripheral (SpO$_2$) and/or regional oxygenation level), an amount of carbon dioxide in the patient's 106 breath (e.g., a capnograph and/or end tidal CO$_2$ (EtCO$_2$)), a heart rate of the patient 106, a blood pressure of the patient 106, a carboxyhemoglobin level of the patient's 106 blood, a temperature of the patient 106, a respiration rate of the patient 106, and a pulse rate of the patient 106.

In some examples, the medical device 108 includes one or more therapy circuits, one or more mechanical devices, or any combination thereof, which are configured to administer a therapy to the patient 106. For example, the medical device 108 can include a discharge circuit that outputs an electrical signal to electrodes disposed on the chest of the patient 106. In some cases, the electrical signal is in the form of a defibrillation shock, a pacing signal, or a synchronized cardioversion signal.

The medical device 108 further includes a speaker 110 configured to output an audible marker 112 into the rescue scene 102. The audible marker 112 is a sound output by the speaker 110 of the medical device 108. Examples of the audible marker 112 include a start-up sound of the medical device 108 (e.g., a sound that the medical device 108 outputs when the medical device 108 powers up), a shut-down sound of the medical device 108 (e.g., a sound that the medical device 108 outputs when the medical device 108 turns off), an audible prompt output by the medical device 108 (e.g., an instruction output by the medical device 108 to the rescuer 104 related to care of the patient 106), an alarm output by the medical device 108, or any other type of sound output by the medical device 108. In some implementations, the medical device 108 outputs the audible marker 112 multiple times (e.g., periodically), to allow for multiple opportunities for synchronization during the rescue event. The audible marker 112 is a predetermined sound, in some cases. As used herein, the term "audible prompt," and its equivalents, may refer to a sound that instructs a user to perform an action in furtherance of treating a patient. For example, the medical device 108 outputs an audible prompt instructing the rescuer 104 to check a placement of electrodes on the chest of the patient 106, to remove hands from the patient 106 before a defibrillation shock is administered to the patient 106 by the medical device 108, or to administer the defibrillation shock to the patient 106. As used herein, the term "alarm," and its equivalents, may refer to a condition of a device or patient that has crossed at least one predetermined threshold. For example, the medical device 108 may output an audible alarm if the heart rate of the patient 106 is above a first threshold or below a second threshold. Although not specifically illustrated in FIG. 1, in some cases, the audible marker 112 is another type of sound output by the medical device 108, such as a sound of an electrical shock output by the medical device 108 for defibrillating the patient 106. According to some implementations, the spectral content of the audible marker 112 is configured to be discernible in noisy environments (e.g., environments with greater than a threshold noise level). For instance, the audible marker 112 includes multiple harmonics of a base audio signal, such that even if the base audio signal is masked by ambient sound in the rescue scene 102, the harmonics are unlikely to also be masked by the ambient sound. Examples of such spectral content is described in U.S. Pub. No. 2020/0009495, which is incorporated by reference herein in its entirety. In some cases, the audible marker 112 is not perceptible by human hearing. For instance, the audible marker 112 is a sound below 20 Hz and/or above 20 kHz. Accordingly, the audible marker 112 can be prevented from distracting the rescuer 104.

The audible marker 112 is output into the rescue scene 102 and detected by a recorder 114. The recorder 114, for example, includes a microphone configured to detect sound. In some examples, the recorder 114 is a computing device, such as a mobile phone, wearable device, or the like. The recorder 114 is carried by, or otherwise associated with, the rescuer 104 in some implementations.

The recorder 114 is separate from the medical device 108. Integrating a recorder into medical devices, such as defibrillators, is challenging and expensive. For example, such an integrated recorder generates a significant amount of data that would take up a data processing channel of the medical device 108. Further, the medical device 108 generates various sounds (e.g., the audible marker 112) that are difficult to shield from an integrated recorder. Furthermore, delicate electronics in an integrated recorder are difficult to electrically isolate from circuitry in medical devices, particularly medical devices configured to output high-energy electrical signals like defibrillation shocks. By keeping the recorder 114 separate from the medical device 108, the mechanical and electrical design of the medical device 108 can be simplified. In some implementations, the recorder 114 refrains from, or is incapable of, directly communicating with the medical device 108.

In various implementations, the recorder 114 also detects other types of sound in the rescue scene 102. For instance, the recorder 114 also detects a voice of the patient 106, the rescuer 104, or both. The rescuer 104, for example, audibly narrates the results of diagnostic tests and/or treatments performed on the patient 106. That is, the rescuer 104 can make voice notations that are detected by the recorder 114. For instance, the rescuer 104 remarks out loud that "a sedative has been administered" to the patient 106 prior to intubation. The rescuer 104, in some cases, narrates observations of the patient 106 and the rescue scene 102. For instance, the rescuer remarks that the patient 106 is "unresponsive." The recorder 114 also detects any sounds made by the rescuer 104 that are not specifically directed to the recorder 114 or treating the patient 102. In some examples, the recorder 114 detects conversations, orders, or other types of voice notations between the rescuer 104 and other individuals at the rescue scene 102. Various sounds that are spoken by the patient 106, the rescuer 104, or other individuals are detected by the recorder 114.

The recorder 114 generates a recording file 116 based on the sound in the rescue scene 102. As used herein, the term "file" and its equivalents may refer to a collection of data stored in a single unit. In some cases, each file is identified by a file name. The medical device 108 generates a parameter file 118 based on one or more physiological parameters of the patient 106. In some cases, the parameter file 118 includes data indicating physiological parameter(s) of the patient 106 over time. For instance, the parameter file 118 includes values of the physiological parameter(s). The parameter file 118, in some cases, also indicates when the audible marker 112 was output by the medical device 108. In various implementations, it is advantageous to synchronize the recording file 116 and the parameter file 118. For example, a voice notation by the rescuer 104 indicates a symptom of the patient 106 at a particular time. If the physiological parameter(s) of the patient 106 at the particular time are also known, a care provider 120 may be able to accurately diagnose a condition experienced by the patient 106 at the rescue scene 102.

The recorder 114 transmits the recording file 116 to a synchronizer 122. In addition, the medical device 108 transmits the parameter file 118 to the synchronizer 122. The synchronizer includes hardware (e.g., a processor configured to perform operations), software (e.g., instructions stored in memory that, when executed by a processor, cause the processor to perform operations), or both. In various implementations, the synchronizer 122 includes one or more computing device configured to execute software instructions. In some cases, the recording file 116 and/or the parameter file 118 are transmitted over one or more intermediary communication networks, such as at least one wired network (e.g., an electrical cable and/or an optical cable) and/or one or more wireless networks (e.g., a BLUETOOTH® network; a near field communication (NFC) network; a WI-FI® network; a $3^{rd}$ Generation Partnership Project (3GPP) network, such as a Long Term Evolution (LTE) or New Radio (NR) radio access network (RAN); etc.).

The synchronizer 122 is configured to align the sound recorded in the recording file 116 with the parameter(s) indicated in the parameter file 118. In particular, the synchronizer 122 is configured to detect the audible marker 112 recorded in the recording file 116. Once the audible marker 112 is detected, the synchronizer 122 generates aligned data 124 by time-aligning the parameter(s) in the parameter file 116 with the recording in the recording file 116. The aligned data 124, for example, includes at least two data channels: one channel including the sound recorded by the recorder 114 and another channel including the parameter(s) detected by the medical device 108. In some examples, the synchronizer 122 outputs the aligned data 124 to a playback device 126. The playback device 126, for example, is a computing device configured to output an indication of the parameter(s) while also outputting the time-aligned recorded sound. The indication of the parameter(s) is a video of waveforms of the parameter(s), in some cases. For example, the playback device 126 outputs the parameter(s) and the recorded sound to a user performing post-event review of the patient 106 at the rescue scene 102.

In some implementations, the synchronizer 122 performs further analysis on the aligned data 124. For example, the synchronizer 122 includes a speech-to-text functionality that converts the recorded voice of the rescuer 104 into a readable text file. In some implementations, the synchronizer 122 recognizes audible commands issued by the rescuer 104 in the rescue scene 102 using voice recognition techniques. In some implementations, the synchronizer 122 automatically identifies a suspected condition of the patient 106 based on the recording file 116 and/or the parameter file 118. The synchronizer 122 generates a report 128 based on the results of the analysis. For example, the report 128 includes the parameter(s) detected by the medical device 108, the recorded sound detected by the recorder 114, a text version of the voice of the rescuer 104, commands issued by the rescuer 104, a suspected condition of the patient 106, or any combination thereof. In various implementations, the report 128 further indicates the times at which different events occurred at the rescue scene 100. For example, the report 128 indicates when the parameter(s) were detected by the medical device 108, when the rescuer 104 observed something about the patient 106 (e.g., that the patient was unresponsive), when the rescuer 104 administered a treatment to the patient 106 (e.g., when the patient was administered the sedative), or other events discernable based on the recording file 116 and/or the parameter file 118.

In various implementations, the synchronizer 122 performs speech-to-text on the recording file 116 and/or the aligned data 124. For example, the synchronizer 122 includes, stores, or otherwise utilizes a Hidden Markov Model (HMM), a dynamic time warping (DTVV) model, one or more neural networks, or any combination thereof, to identify spoken words in the recording file 116 and/or the aligned data 124. In some cases, the synchronizer 122 generates text data based on the words captured in the recording file 116 and/or the aligned data 124. The text data, for example, is included or otherwise used to generate the report 128.

The synchronizer 122 outputs the report 128 to a clinical device 130, for example. In various implementations, the clinical device 130 is a computing device configured to output at least a portion of the report 128 to the care provider 120 or to another user. Accordingly, the care provider 120 is provided additional context about the patient 106. In some cases, the report 128 enhances the care provider's 120 understanding of the condition of the patient 106 before the patient 106 is transferred to the care provider 120 for additional care.

Although the foregoing description of FIG. 1 provides an example in which a physiological parameter of the patient 106 is aligned with an audio recording of the rescue scene, implementations are not so limited. Similar techniques can be utilized to align other types of data. In some examples, a system analyzes an audio recording of a crime scene to identify the sound of a gunshot and, in response to the sound of the gun shot, to automatically notify a law enforcement agency. In some instances, a system analyzes an audio recording of respiration sounds of a patient being ventilated (e.g., using a bag-valve mask) and determines a respiratory rate of the patient (e.g., even if a $CO_2$ sensor, which may normally detect the respiratory rate, may not detect $CO_2$ from the patient's airway).

In particular examples, an in-vehicle sensor is installed in a vehicle (e.g., a car, a plane, a bus, a train, or the like) and is configured to detect a parameter of the vehicle. For instance, the sensor detects an acceleration or speed of the vehicle. In addition, a computing device (e.g., a mobile phone) is located in the vehicle and detects audio within the vehicle. The vehicle experiences an event (e.g., a crash or collision) while the in-vehicle sensor is detecting the parameter and the computing device is detecting the audio. Using similar techniques to those described above, the parameter detected by the in-vehicle sensor and the audio detected by the computing device is aligned for post-event review. In some cases, the synchronizer 122 detects the event based on the recorded parameter and the audio recording. For instance, an abrupt change in acceleration detected by the in-vehicle sensor is indicative of a crash, and a sound in the audio recording indicating the crash may also be identified using signal processing techniques. Alternatively, the in-vehicle sensor outputs a known sound that is detected in the audio recording. The synchronizer 122 aligns the recorded parameter and the audio recording. In some cases, the aligned parameter and audio recording can be viewed for post-event review. For example, a user may review aligned data from a crash experienced by a driver to determine whether the driver was distracted prior to the crash to indicate whether the driver was at fault for the crash, or may identify if other sounds indicative of other factors (e.g., a portion of the vehicle failing prior to the crash) may indicate that the driver was not at fault for the crash. The aligned data 124 and/or report 128 reflecting the recording file 116 and parameter file 118 detected during the crash can be transmitted to various devices for playback and/or post-event review.

Although FIG. 1 has been described with respect to a single parameter file and a single recording file, implementations are not so limited. In some cases, the synchronizer 122 receives multiple parameter files and multiple recording files from various medical devices and recording devices. For example, the synchronizer 122 receives recorded parameters and audio recordings from multiple devices in a fleet associated with an EMS organization, which includes multiple rescuers responding to various rescue scenes. The synchronizer 122 is configured to match a parameter file with a corresponding recording file based on detecting audible prompts in the recording file. For example, the synchronizer 122 receives a first parameter file indicating an event in which a first medical device output a start-up sound and a defibrillation shock sound separated by time period a, and also receives a second parameter file indicating an event in which a second medical device output a start-up sound and a defibrillation shock sound separated by time period b, wherein a is different than b. The synchronizer 122 identifies the start-up sounds and defibrillation shock sounds in a first recording file and a second recording file. By determining that the start-up sound and defibrillation shock sound in the first recording file are separated by time period a, the synchronizer 122 determines that the first recording file is associated with the first parameter file (and not the second parameter file). Furthermore, by determining that the start-up sound and defibrillation shock in the second recording file are separated by time period b, the synchronizer 122 determines that the second recording file is associated with the second parameter file (and not the first parameter file). Thus, various implementations described herein further enable the synchronizer 122 to match recorded parameters and audio recordings associated with the same events.

In some cases, the synchronizer 122 receives multiple parameter files 118 and/or multiple recording 116 files obtained from a single rescue scene. For instance, the recording files 116 are obtained from multiple recorders 114 in the rescue scene 102. The synchronizer aligns the multiple parameter files 118 and/or multiple recording files 116. According to some implementations, the synchronizer 122 generates the aligned data 124 to include the multiple parameter files 118 and/or multiple recording files 116. The synchronizer 122, in various instances, combines the multiple recording files 116 into a single audio file. The single audio file provides a surround-sound perspective of the rescue scene when played by the playback device 126, in some cases. According to some implementations, the synchronizer 122 includes one or more machine learning models configured to enhance a first recording file 116 based on a second recording file 116 and aligns the enhanced first recording file 116 with the parameter file 118. In some cases, the synchronizer 122 removes noise or interference from the first recording file 116 based on the second recording file 116.

In various implementations, similar techniques to those described with respect to FIG. 1 can be used to align a video file with the parameter file 118. For example, the recording file 116 includes a video obtained by the recorder 114 of the rescue scene 102. Instead of or in addition to the audible marker 112, the medical device 108 outputs a visual marker that is depicted in the recording file 116 and indicated in the parameter file 118. The synchronizer 122, in various implementations, generates the aligned data 124 by time-aligning the recording file 116 and the parameter file 118 based on detecting the audible marker 112 and/or the visual marker in the recording file 116.

In various cases, the synchronizer 122 aligns parameter files 118 generated by multiple medical devices 108. For instance, the synchronizer 122 aligns parameter files 118 generated by a mechanical chest compression device, a CPR sensor, a ventilator, a video laryngoscope, an ultrasound imaging system, a cerebral oximeter, or some other type of monitor configured to detect a parameter of the patient 106.

According to some implementations, the synchronizer 122 may detect various other features within the recording file 116. In some cases, the medical device 108 (e.g., a glucometer) outputs a sound encoding a numerical result of a parameter detected from the patient 106. The synchronizer 122, in some cases, identifies the numerical result by analyzing the recording file 116, and includes the numerical result in the report 128. In various cases, the medical device 108 outputs other sounds that are clinically relevant and captured in the recording file 116. For example, a video laryngoscope makes a sound indicative of the application of force on the patient 106 during use, an infusion pump generates a particular sound when it administers an intravenous drug to the patient 106, or the like. The synchronizer 122 detects a sound output by the medical device 108 in the recording file 116 and indicates the associated clinically relevant information in the report 128, in various cases. In some examples, the medical device 108 outputs a sound indicative of an identifier (e.g., a serial number) associated with the patient 106 and/or the medical device 108, the synchronizer 122 identifies the identifier based on the recording file 116, and indicates the identifier in the report 128 or verifies that the parameter file 118 corresponds to the recording file 116 based on the identifier. In some implementations, the synchronizer 122 identifies clinically relevant sounds output by the patient 106. For instance, the synchronizer 122 detects agonal respirations (a sound made while in cardiac arrest, particularly early in the arrest, and is known to be associated with increased patient viability or likelihood of survival) in the recording file 116 and indicates the agonal respirations in the report 128.

In some cases, the recorder 114 implements a "tap-to-talk" functionality. According to various implementations, the recorder 114 is configured to capture a short (e.g., a 5 second, 10 second, 30 second, etc.) audio recording in response to receiving an input signal from a user (e.g., the rescuer 104 presses a button of the recorder 114 or the rescuer 104 taps a user interface element output on a touchscreen of the recorder 114). The rescuer 104 verbally announces an event during the capture period of the recorder 114. In some cases, the short audio recording is included in the recording file 116. The recorder 114 provides the audio recording to the synchronizer 122. The synchronizer 122 identifies the announced event (e.g., using speech-to-text)

and includes an indication of the announced event in the report 128. In various implementations, the synchronizer aligns the short audio recording with the parameter file 118, such that the report 128 indicates the announced event is also associated with one or more parameters detected contemporaneously with the announced event at the rescue scene 102.

In various implementations, a similar environment to the one illustrated in FIG. 1 can be used to synchronize video data captured by a camera of the recorder 114. For instance, the video data is at least a portion of the recording file 116, and is aligned with the parameter file 118 by the synchronizer 122 using various techniques described herein. In some cases, a visible marker is used as an alternative (or in addition to) the audible marker 112 to align the parameter file 118 and the recording file 116. For instance, the medical device 108 includes a display, light source, or other output device configured to output a light-based visible marker to the recorder 114. For instance, the visible marker may include an icon displayed by the medical device 108, a flashing-light pattern output by the medical device 108, or the like. The recorder 114, in some implementations, further includes a camera and/or light sensor configured to detect the visible marker. The synchronizer 122 utilizes the visible marker detected by the recorder 114 to align the parameter file 118 and the recording file 116, for instance. In some cases, the visible marker includes a light-based signal that imperceptible to the rescuer 104 (e.g., the visible marker is output in a direction that does not intersect with the visual field of the rescuer 104, wherein the direction may be different than a direction in which the medical device 108 outputs a visual instruction to the rescuer 104). Accordingly, the visible marker can be prevented from distracting the rescuer 104.

In some implementations, the recorder 114 is and/or includes another medical device configured to detect one or more additional parameters of the patient 106. For instance, the recorder 114 includes a mechanical chest compression device, a CPR sensor (configured to detect manual chest compressions administered by the rescuer 104), a ventilator, a video laryngoscope, a cerebral oximeter, an ultrasound imaging system, or a head-up CPR device. Various techniques described herein can be used to align the parameter(s) detected by the medical device 108 with parameter(s) detected by the recorder 114.

In some cases, an additional device associated with the patient 106 is configured to output a sound that is detected by the recorder 114, wherein the sound itself encodes data relevant to managing care of the patient 106. For instance, a glucometer detecting a level of glucose in the blood of the patient 106 emits a sound that encodes the level of the glucose in the sound itself. The recorder 114 may indicate the time at which the sound was detected in the recording file 116, as well as an indication of the sound. The synchronizer 122 is configured to decode the sound, thereby identifying the level of the glucose as well as the time at which the level of the glucose was detected. In various implementations, the synchronizer 122 indicates the level of the glucose in the aligned data 124 and/or the report 128. Implementations are not limited to glucometers and glucose levels, and can include any other secondary medical device that detects a physiological parameter and/or administers a therapy to the patient 106, wherein the sound emitted by the secondary device encodes the physiological parameter and/or a parameter of the therapy. For example, a suction device and/or a mechanical chest compression device may emit a sound indicating that a chest compression is administered by the device, a force of the chest compression administered by the device, a frequency of chest compressions administered by the device, or a position of a chest compression administered by the device. In particular cases, a video laryngoscope emits a sound indicative of a force applied by the video laryngoscope, which could be used to discern a time at which the patient 106 is intubated (or a time at which individual intubation attempts and/or events were performed). In some cases, an infusion pump emits a sound indicative of a medication administered by the pump to the patient 106.

In some implementations, the patient 106 is associated with a particular identifier (e.g., a number uniquely associated with the patient 106 and not other patients). In some cases, the medical device 108 generates the identifier when the medical device 108 begins to monitor and/or treat the patient 106. The audible marker 112, in some cases, encodes the identifier. The recording file 116 may further indicate the identifier of the patient 106. The parameter file 118 may indicate the identifier. Accordingly, the synchronizer 122 may indicate the identifier in the aligned data 124 and/or the report 128. In some cases, the synchronizer 122 determines that the recording file 116 and the parameter file 118 are associated with the same patient 106 based on the identifier.

In some cases, the recorder 114 detects a sound from the patient 106 and indicates the sound in the recording file 116. For instance, the recorder 114 detects agonal respiration(s) of the patient 106. Agonal respiration(s) may be associated with the patient 106 being in an early stage of cardiac arrest. In some cases, the synchronizer 122 indicates the sound, or a condition associated with the sound, in the aligned data 124 and/or the report 128. For instance, by identifying agonal respiration(s), the care provider 120 may be enabled to treat the patient 106 in the early stage of cardiac arrest, which can enhance the prognosis of the patient 106.

According to some examples, the medical device 108 emits the audible marker 112 multiple times during use. Thus, if the recorder 114 is not recording at a particular time during the care event of the patient 106 (e.g., when the medical device 108 is powered on), then the synchronizer 122 may nevertheless align the recording file 116 and the parameter file 118.

In various cases, the synchronizer 122 is configured to recognize an identity of the rescuer 104 based on the voice of the rescuer 104 indicated in the recording file 116. For instance, the synchronizer is configured to access a database storing voice parameters (e.g., spectral signatures) of multiple rescuers in an EMS system. The synchronizer 122, in some cases, is configured to identify the rescuer 104 by comparing at least a portion of the recording file 116 to the entries in the database. In various cases, the synchronizer 122 indicates the identity of the rescuer 104 in the aligned data 124 and/or the report 128.

Figure 2:
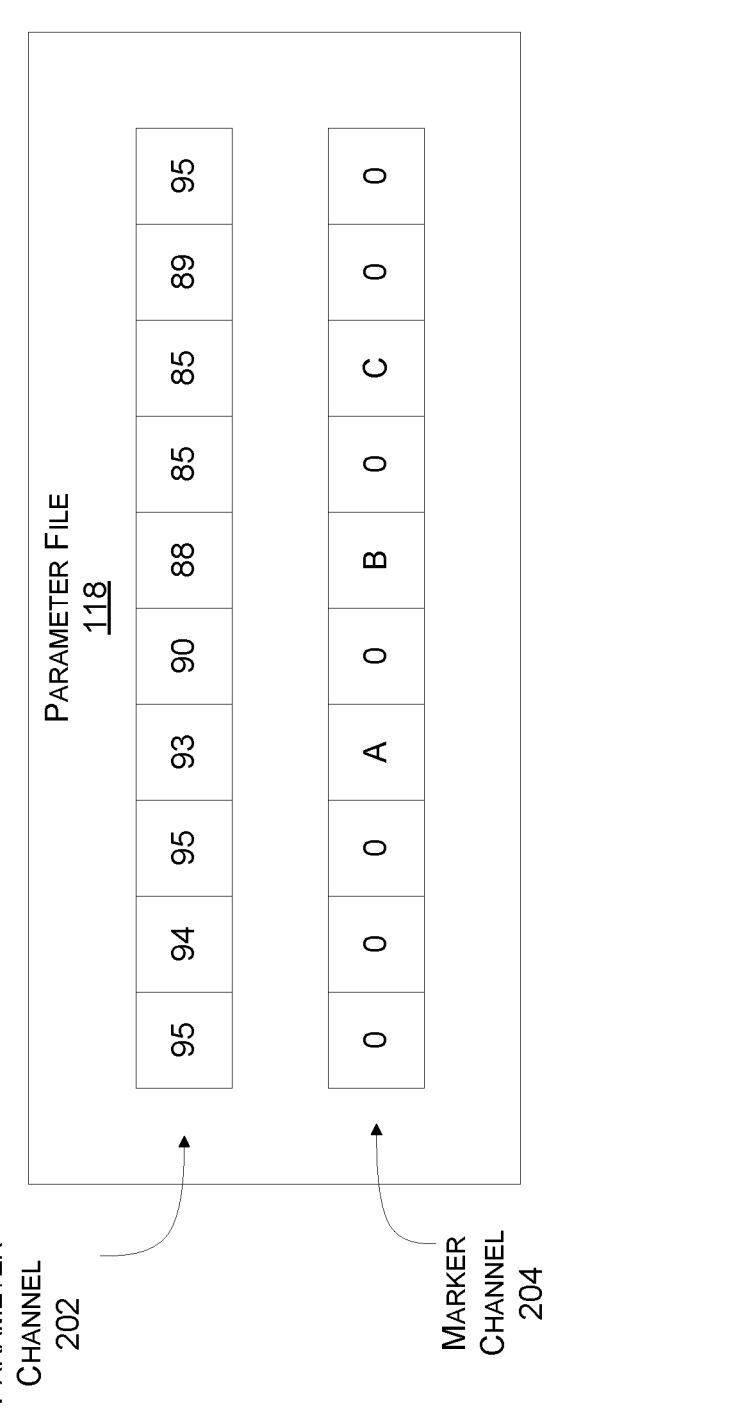
FIG. 2 illustrates an example of a parameter file described with reference to FIG. 1.

FIG. 2 illustrates an example of the parameter file 118 described above with reference to FIG. 1. In FIG. 2, time increases from left to right. The parameter file 118 includes two channels: a parameter channel 202 and a marker channel 204. The parameter channel 202 includes values of a parameter, such as values of a physiological parameter of the patient 106. The values of the parameter in the parameter channel 202 are detected by the medical device 108 at a particular sampling frequency, such as once a minute, five times a minute, 10 times a minute, 30 times a minute, once a second, or multiple times per second. That is, the values of the parameter in the parameter channel 202 are sampled at discrete (sampling) times. The values in the parameter channel 202 are the sampled parameter values. Although various types of parameters are possible in various implementations in the present disclosure, FIG. 2 illustrates an example of pulse oxygenation values of the patient 106 that are detected by the medical device 108 over a particular time interval.

The marker channel 204 includes data indicating various audible markers output by the medical device 108 during the time interval. For instance, in the example of FIG. 2, the medical device 108 outputs three audible markers: audible marker "A," audible marker "B," and audible marker "C." In various implementations, the parameter channel 202 and the marker channel 204 are time-aligned, such that the parameter file 118 indicates what parameter values were detected as the audible markers were output by the medical device 108. For example, the pulse oxygenation value of the patient 106 was "93" when audible marker "A" was output into the rescue scene 102, the pulse oxygenation value of the patient 106 was "88" when audible marker "B" was output into the rescue scene 102, and the pulse oxygenation value of the patient 106 was "85" when the audible marker "C" was output into the rescue scene 102. Although not illustrated in FIG. 2, in some cases, the parameter file 118 further includes a third channel indicating timestamps indicating when the various values of the parameter channel 202 were detected and the audible markers of the marker channel 204 were output into the rescue scene 102.

Figure 3:
FIG. 3 illustrates an example of a recording file described with reference to FIG. 1.

FIG. 3 illustrates an example of the recording file 116 described above with reference to FIG. 1. In FIG. 3, time increases from left to right. In the example of FIG. 3, the recording file 116 includes a single channel: an audio recording 302. In some cases, the recording file 116 includes a second channel that includes timestamps aligned with the audio recording 302. In cases where both the parameter file 118 and the recording file 116 include timestamps, the timestamps of the parameter file 118 may be different than the timestamps in the recording file 116, because the parameter file 118 and the recording file 116 are generated by different devices that have different internal clocks and do not communicate with each other.

As shown, the audio recording 302 includes discrete audio samples (D1 to D15) of sound in the rescue scene 102 taken at a particular sampling rate (i.e., at discrete times). The sampling rate of the recording file 116 is, in some cases, different than the sampling rate of the parameter file 118. In various implementations, the audio recording 302 includes detected markers 304 in three respective audio samples: D9, D11, and D13. The three detected markers 304 correspond to the three audible markers output by the medical device 108 and indicated in the marker channel 204.

Figure 4:
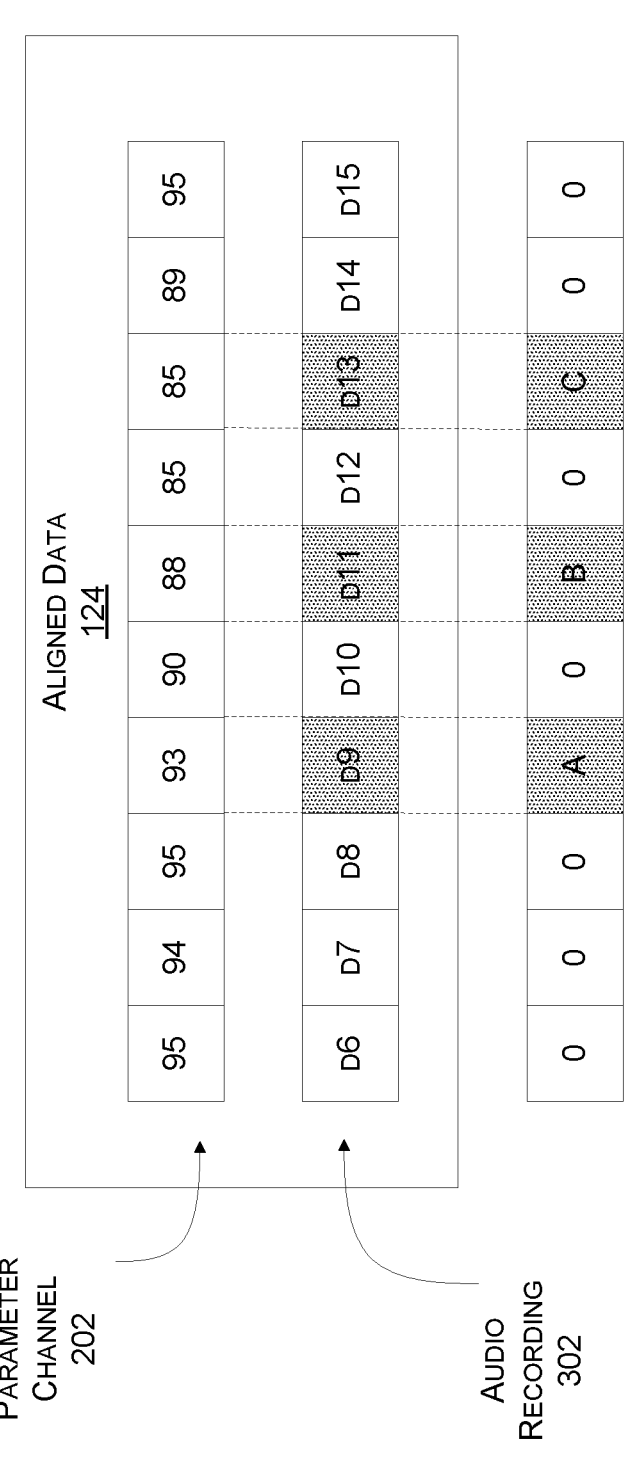
FIG. 4 illustrates an example of aligned data described with reference to FIG. 1.

FIG. 4 illustrates an example of the aligned data 124 described above with reference to FIG. 1. In FIG. 4, time increases from left to right. The aligned data 124 includes two channels: the parameter channel 202 of FIG. 2 and the audio recording 302 of FIG. 3. For reference, the marker channel 304 is also depicted in FIG. 4 to show the alignment between the parameter channel 202 and the audio recording 302.

Audible marker "A" is detected in audio sample D9, audible marker "B" is detected in audio sample D11, and audible marker "C" is detected in audio sample D13. Accordingly, audio sample D9 is aligned with the parameter value "93," audio sample D11 is aligned with parameter value "88," and audio sample D13 is aligned with parameter value "85." Notably, the parameter channel 202 and the audio recording 302 originally had different lengths. Accordingly, in some cases, the longer of the two (the audio recording 302) is edited to ensure that both channels in the aligned data 124 have the same length.

Although FIGS. 2-4 illustrate examples in which the parameter channel 202, the marker channel 204, and the audio recording 302 are obtained with the same sampling rate, implementations are not so limited. For example, in examples in which the parameter channel 202 and the audio recording have different sampling rates, they can nevertheless be aligned as long as their respective sampling rates are known. In some cases, the sampling rates are included in the parameter file 118 and recording file 116, respectively. In some cases, the synchronizer 122 infers the sampling rate of the parameter file 118 and/or the recording file 116 based on a file type of the parameter file 118 and/or recording file 116. For example, if the recording file 116 is an MP3 file, the synchronizer 122 may infer that the recording file 116 has a sampling rate associated with the MP3 file format (e.g., 48 kHz).

Figure 5:
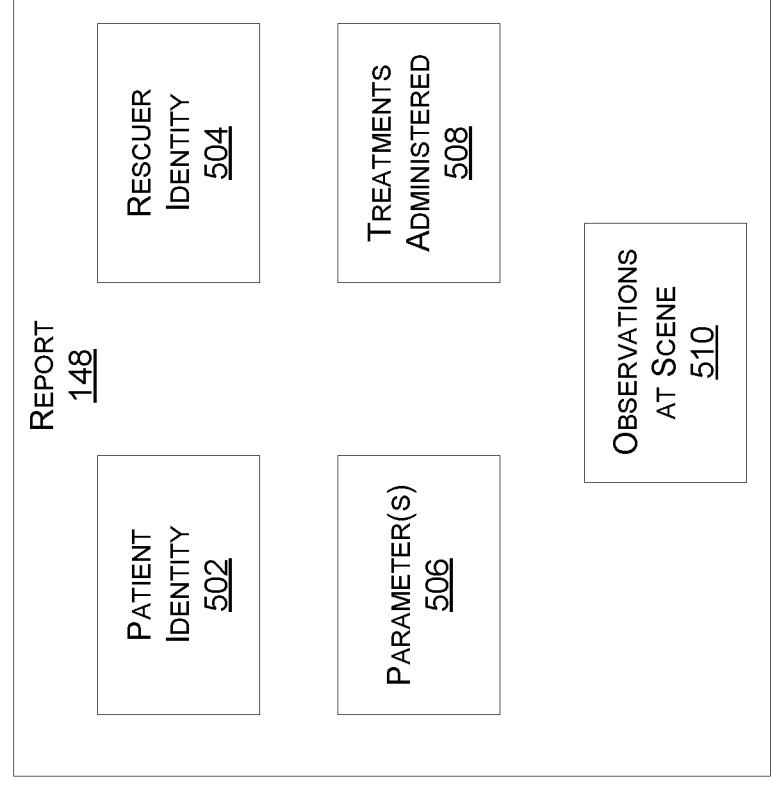
FIG. 5 illustrates an example of a report described with reference to FIG. 1.

FIG. 5 illustrates an example of the report 148 described above with reference to FIG. 1. In various implementations, the report 148 includes a patient identity 502, a rescuer identity 504, one or more parameters 506, one or more treatments administered 508, and observations at the rescue scene 510. In some cases, at least one of the patient identity 502, the rescuer identity 504, the parameter(s) 506, the treatment(s) administered 508, and the observations at the rescue scene 510 is omitted from the report 148.

The patient identity 502 indicates a patient (e.g., the patient 106) being treated by a rescuer and/or medical device at a rescue scene. In some examples, the patient identity 502 is uniquely specific to the patient. For example, an EMS team treats multiple patients, but the patient specified in the report 148 is the only patient with the patient identity 502. In various cases, the patient identity 502 is a name of the patient, an identifier of the patient (e.g., a string and/or number uniquely assigned to the patient), or one or more characteristics of the patient (e.g., where the patient was found, demographic information of the patient, etc.). The patient identity 502 is input into the medical device at the rescue scene, in various implementations. For example, the rescuer inputs the patient identity 502 into the medical device at the rescue scene.

The rescuer identity 504 indicates the rescuer (e.g., the rescuer 104) attending to the patient at the rescue scene. The rescuer identity 504 is uniquely specific to the rescuer. For example, the EMS team includes multiple rescuers, but only the rescuer attending to the patient has the specific rescuer identity 504. In various cases, the rescuer identity 504 is a name of the rescuer, an identifier of the patient (e.g., a string and/or number uniquely assigned to the rescuer). In some examples, the rescuer identity 504 is input into the medical device by the rescuer.

The parameter(s) 506 include one or more physiological parameters detected from the patient at the rescue scene. In some cases, the parameter(s) 506 are detected by the medical device. In various cases, the parameter(s) 506 are derived based on the parameter file generated by the medical device at the rescue scene. According to some implementations, the parameter(s) 506 further specify the times at which the physiological parameter(s) are detected. For example, the parameter(s) 506 include timestamps indicating the times at which the physiological parameter(s) were detected.

The treatment(s) administered 508 indicate one or more treatments of the patient at the rescue scene. The treatment(s) are administered by the rescuer, in some instances. For example, the treatment(s) administered 508 indicate whether the patient was intubated, administered with a medication (e.g., a sedative, a paralytic, an antibiotic, etc.), defibrillated, or administered with any other type of treatment. In various cases, the treatment(s) administered 508 are input into the medical device by the rescuer at the rescue scene. In some implementations, the treatment(s) administered 508 are identified based on the voice of the rescuer in a recording file of the rescue scene (e.g., the recording file 116). For example, the rescuer verbally explains that the patient is being intubated, a synchronizer (e.g., the synchronizer 122) recognizes the words in the recording file indicating that the patient is being intubated (e.g., using speech-to-text), the synchronizer recognizes the treatment based on the words (e.g., using speech recognition), and the synchronizer generates the treatment(s) administered 508 based on the recognized treatment. In some implementations, the treatment(s) administered 508 further indicate the time(s) at which the treatment(s) occurred. For instance, the synchronizer identifies the time at which the patient is intubated based on aligning the recording file with a parameter file and comparing the relative time at which the rescuer spoke the words indicating the treatment in the recording file and the relative time at which parameter was detected in the parameter file.

The observations at the rescue scene 510 indicate other information about the rescue scene. The observations at the rescue scene 510 are input by the rescuer and/or derived (e.g., by the synchronizer) from the voice of the rescuer in the recording file of the rescue scene. In some cases, the observations at the rescue scene 510 indicate a condition of the patient at the rescue scene (e.g., disoriented, unresponsive, etc.) or a result of a diagnostic test performed at the rescue scene (e.g., a blood glucose level of the patient measured at the rescue scene). In some cases, the observations at the rescue scene 510 further indicate the times at which the observations at the rescue scene 510 were made.

Figure 6:
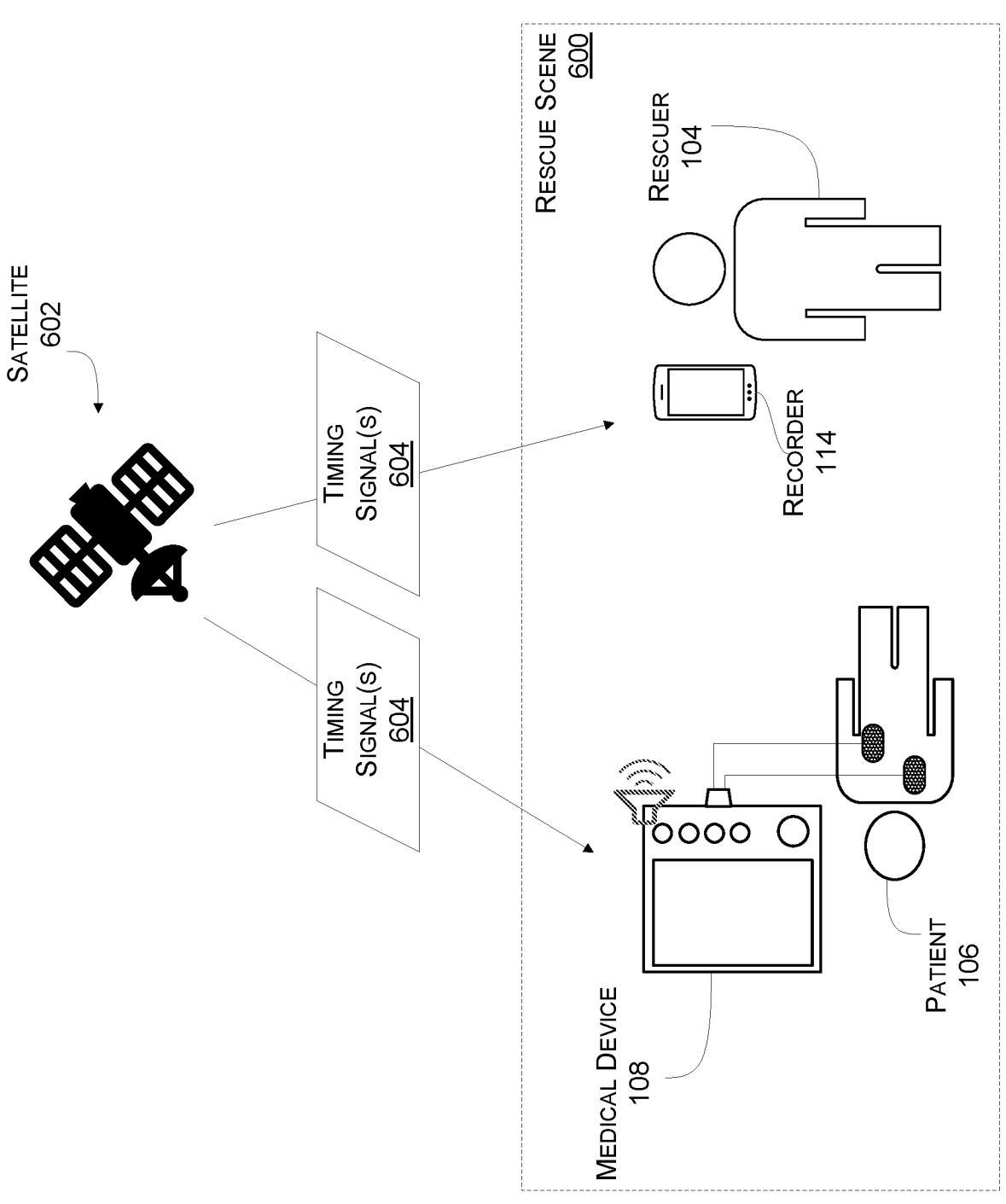
FIG. 6 illustrates an example rescue scene associated with an alternate technique for aligning a recording file and a parameter file obtained by the medical device.

FIG. 6 illustrates an example rescue scene 600 associated with an alternate technique for aligning a recording file and a parameter file obtained by the medical device 108. As illustrated, the rescue scene 600 further includes the rescuer 104, the patient 106, and the recorder 114 described above with reference to FIG. 1.

FIG. 6 further includes a satellite 602 that transmits at least one timing signal 604 to the medical device 108 and to the recorder 114. The satellite 602, for example, is a device that is in the earth's orbit and configured to transmit signals to one or more receivers disposed on the surface of the earth. The timing signal(s) 604 are transmitted wirelessly to the medical device 108 and to the recorder 114. For example, the timing signal(s) 604 are electromagnetic (e.g., radio frequency) signals that encode information. The timing signal(s) are broadcast from the satellite 602, for example. Although only a single satellite 602 is illustrated in FIG. 6, in some cases, multiple satellites including the satellite 602 transmit respective timing signals to the medical device 108 and to the recorder 114.

The medical device 108 and the recorder 114 are independent computing devices with respective receivers configured to receive the timing signal(s) 604 and respective processors configured to analyze the timing signal(s) 604. Based on information encoded in the timing signal(s) 604, the medical device 108 and the recorder 114 are able to recognize a consistent time scale. Thus, when the medical device 108 generates a parameter file (e.g., the parameter file 118) and the recorder 114 generates a recording file (e.g., the recording file 116), both the parameter file and the recording file can indicate a consistent time scale. In some cases, the parameter file includes timestamps and the recording file includes timestamps. Accordingly, a synchronizer (e.g., the synchronizer 122) aligns the parameter file and the recording file by matching or otherwise aligning the respective timestamps in the parameter file and the recording file.

In various implementations, the satellite 602 is part of a location service system. For example, the satellite 602 is a Global Positioning System (GPS) satellite and the timing signal(s) 604 are GPS signal(s). In some implementations, the satellite 602 is a Global Navigation Satellite System (GLONASS) satellite, a BeiDou Navigation satellite, a Galileo positioning system satellite, an Indian Regional Navigation Satellite System (IRNSS) satellite, or a Quasi-Zenith Satellite System (QZSS) satellite. In some examples, the satellite 602 is a Starlink™ satellite. In particular cases, the satellite 602 is configured to detect its own position and the time at which the timing signal(s) 604 are transmitted. The satellite 602 includes a time of transmission (TOT) of the timing signal(s) 604 in the timing signal(s) 604 themselves. In some cases, the medical device 108 and the recorder 114 adopt the TOT of the timing signal(s) 604 as the times of arrival (TOAs) of the timing signal(s) 604, even though the true TOAs would also be based on the times of flight (TOFs) of the timing signal(s) 604 and could be slightly different between the medical device 108 and the recorder 114 based on their slight differences in location. In some cases, the medical device 108 and the recorder 114 derive the true TOAs based on the TOTs of the timing signal(s) 604. In some examples, the medical device 108 and the recorder generate the timestamps in the parameter file and the recording file based on the TOAs. For instance, the medical device 108 and the recorder 114 respectively calibrate their clocks based on the TOAs and generate the timestamps based on the calibrated clocks.

In particular examples, the medical device 108 or the recorder 114 further determines its location based on the timing signal(s) 604. For example, the medical device 108 or the recorder 114 receives timing signals 604 from multiple satellites 602 and may triangulate its position based on a discrepancy of the timing signals 604 from the individual satellites 602. The medical device 108 or the recorder 114, in some cases, further transmits data indicative of its location to an external device (e.g., an external server) along with the recording file and the parameter file. In various implementations, the external device analyzes the recording file, the parameter file, and the location in accordance with various implementations described herein.

Figure 7:
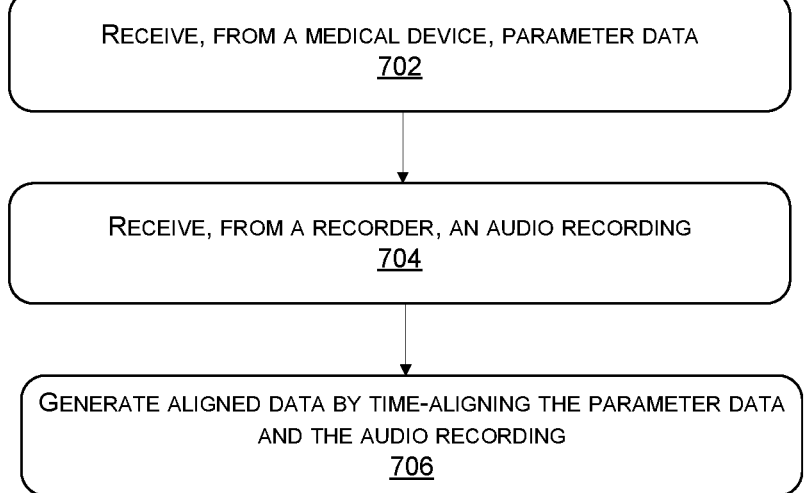
FIG. 7 illustrates an example process for aligning parameter data and an audio recording.

FIG. 7 illustrates an example process 700 for aligning parameter data and an audio recording. The process 700 is performed by an entity, such as the synchronizer 122 described above with reference to FIG. 1.

At 702, the entity receives, from a medical device, parameter data. The parameter data indicates a physiological parameter of a patient, in various implementations. For example, the parameter data includes discrete physiological parameter measurements detected at discrete times, wherein the discrete times correspond to a sampling rate of the medical device. The parameter data indicates the physiological parameter measurements in a first channel (e.g., a "parameter channel"). In some cases, the parameter data includes a second channel (e.g., a "marker channel") that indicates an audible marker output by the medical device. The second channel, for example, indicates the time and/or physiological parameter measurement detected when the audible marker is output by the medical device.

The entity receives the parameter data over a wireless and/or wired interface with the medical device. For instance, the medical device includes a first transceiver and/or a transmitter configured to transmit a signal indicative of the parameter data. The entity includes a second transceiver and/or a receive configured to receive the signal from the medical device. The medical device is, for example, a monitor-defibrillator.

At 704, the entity receives, from a recorder (also referred to as a "recording device"), an audio recording. The audio recording indicates audio sampled at an environment in which the patient was present as the physiological parameter of the patient was detected. For instance, the audio is sampled at a rescue scene in which a rescuer is monitoring and/or treating the patient with the medical device. The audio recording, in some implementations, includes audio sampled at discrete times corresponding to a sampling rate of the recorder. In various examples, the sampling rate of the recorder is different than the sampling rate of the medical device. The sound of the audible marker output by the medical device is indicated in the audio recording, in various cases.

The entity receives the audio recording over a wireless and/or wired interface with the recorder. For example, the recorder includes a third transceiver and/or a transmitter configured to transmit a signal indicative of the audio recording. The entity is configured to receive the signal from the recorder. In various implementations, the recorder is separate from the medical device. For instance, the recorder is incapable of communicating directly with the medical device. In various cases, the recorder includes a mobile device or a standalone recording device.

At 706, the entity generates aligned data by time-aligning the parameter data and the audio record. In various implementations, the entity identifies the sound of the audible marker in the audio recording. Based on identifying the audible marker, the entity generates aligned data by time-aligning the detected physiological parameter measurements and the audio recording. For example, the entity aligns the physiological parameter measurement taken simultaneously as the audible marker was output by the medical device with the audio sample including the sound of the audible marker. The aligned data, in various cases, includes two channels: a first channel including the physiological parameter measurements and a second channel including the audio recording.

In particular implementations, the entity further performs additional actions based on the aligned data. In some cases, the entity outputs the aligned data. For example, the entity includes a screen that visually outputs a waveform representing the physiological parameter measurements and a speaker that audibly outputs the audio recording. In some examples, the entity transmits a signal indicative of the aligned data to an external device, which outputs the aligned data.

According to some cases, the entity generates a report based on the parameter data, the audio recording, the aligned data, or a combination thereof. In some implementations, the entity recognizes one or more words spoken by a rescuer in the audio recording, identifies an event based on the word(s), and indicates the event in the report. For instance, the entity identifies words indicating that the rescuer has intubated the patient, and indicates that the patient was intubated in the report. In some examples, the entity further indicates a time (e.g., a time relative to the physiological parameter measurements and/or audio recording) at which the event occurred. In some implementations, the entity indicates further identifying information about the patient and/or rescuer in the report. The entity outputs the report and/or transmits a signal indicative of the report to an external device.

Figure 8:
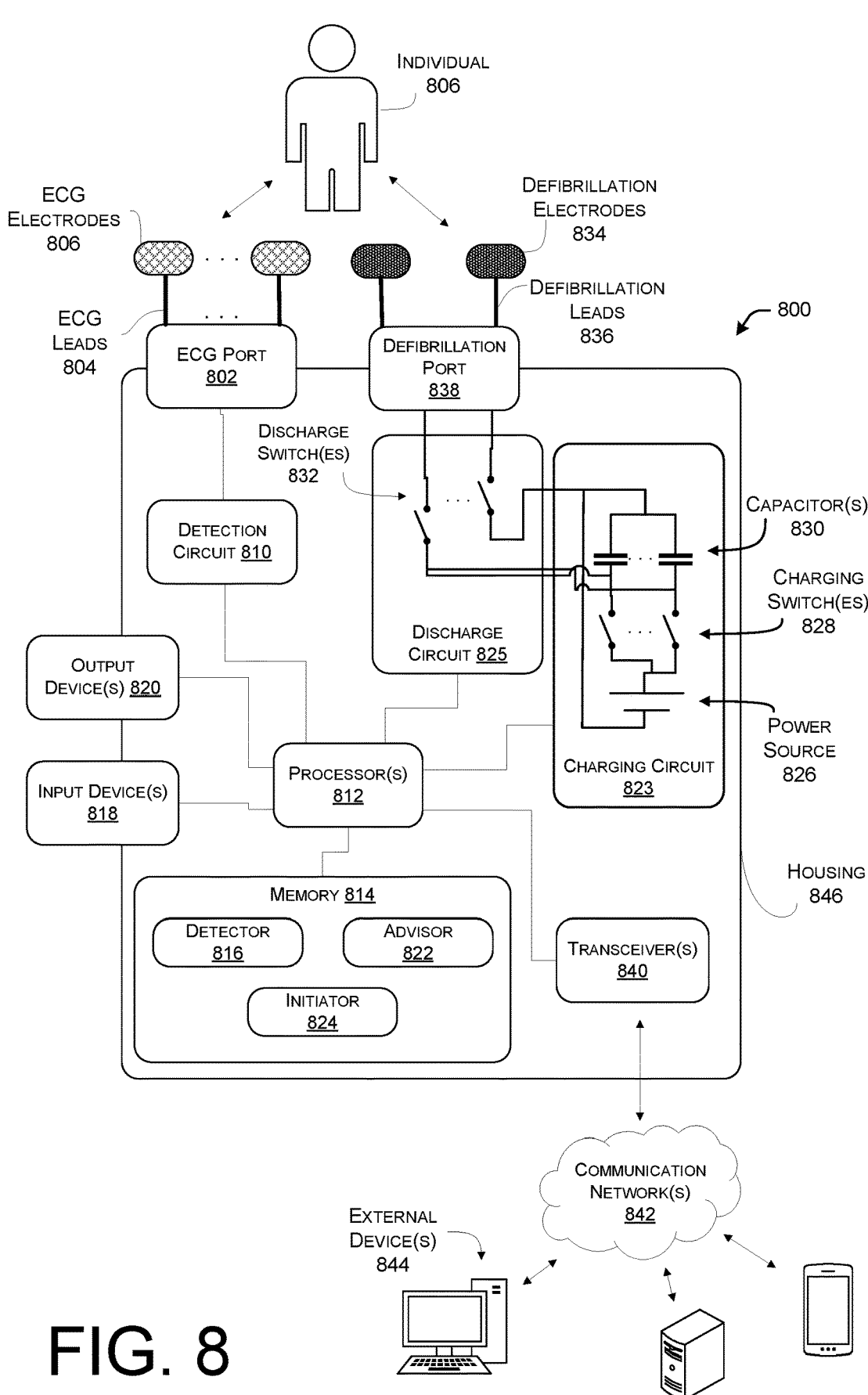
FIG. 8 illustrates an example of an external defibrillator configured to perform various functions described herein.

FIG. 8 illustrates an example of an external defibrillator 800 configured to perform various functions described herein. For example, the external defibrillator 800 is the medical device 106 described above with reference to FIG. 1.

The external defibrillator 800 includes an electrocardiogram (ECG) port 802 connected to multiple ECG leads 804. In some cases, the ECG leads 804 are removeable from the ECG port 802. For instance, the ECG leads 804 are plugged into the ECG port 802. The ECG leads 804 are connected to ECG electrodes 806, respectively. In various implementations, the ECG electrodes 806 are disposed on different locations on an individual 808. A detection circuit 810 is configured to detect relative voltages between the ECG electrodes 806. These voltages are indicative of the electrical activity of the heart of the individual 808.

In various implementations, the ECG electrodes 806 are in contact with the different locations on the skin of the individual 808. In some examples, a first one of the ECG electrodes 806 is placed on the skin between the heart and right arm of the individual 808, a second one of the ECG electrodes 806 is placed on the skin between the heart and left arm of the individual 808, and a third one of the ECG electrodes 806 is placed on the skin between the heart and a leg (either the left leg or the right leg) of the individual 808. In these examples, the detection circuit 808 is configured to measure the relative voltages between the first, second, and third ECG electrodes 806. Respective pairings of the ECG electrodes 806 are referred to as "leads," and the voltages between the pairs of ECG electrodes 806 are known as "lead voltages." In some examples, more than three ECG electrodes 806 are included, such that 5-lead or 12-lead ECG signals are detected by the detection circuit 810.

The detection circuit 810 includes at least one analog circuit, at least one digital circuit, or a combination thereof. The detection circuit 810 receives the analog electrical signals from the ECG electrodes 806, via the ECG port 802 and the ECG leads 804. In some cases, the detection circuit 810 includes one or more analog filters configured to filter noise and/or artifact from the electrical signals. The detection circuit 810 includes an analog-to-digital (ADC) in various examples. The detection circuit 810 generates a digital signal indicative of the analog electrical signals from the ECG electrodes 806. This digital signal can be referred to as an "ECG signal" or an "ECG."

In some cases, the detection circuit 810 further detects an electrical impedance between at least one pair of the ECG electrodes 806. For example, the detection circuit 810 includes, or otherwise controls, a power source that applies a known voltage across a pair of the ECG electrodes 806 and detects a resultant current between the pair of the ECG electrodes 806. The impedance is generated based on the applied voltage and the resultant current. In various cases, the impedance corresponds to respiration of the individual 808, chest compressions performed on the individual 808, and other physiological states of the individual 808. In various examples, the detection circuit 810 includes one or more analog filters configured to filter noise and/or artifact from the resultant current. The detection circuit 810 generates a digital signal indicative of the impedance using an ADC. This digital signal can be referred to as an "impedance signal" or an "impedance."

The detection circuit 810 provides the ECG signal and/or the impedance signal one or more processors 812 in the external defibrillator 800. In some implementations, the processor(s) 812 includes a central processing unit (CPU), a graphics processing unit (GPU), both CPU and GPU, or other processing unit or component known in the art.

The processor(s) 812 is operably connected to memory 814. In various implementations, the memory 812 is volatile (such as random access memory (RAM)), non-volatile (such as read only memory (ROM), flash memory, etc.) or some combination of the two. The memory 814 stores instructions that, when executed by the processor(s) 812, causes the processor(s) 812 to perform various operations. In various examples, the memory 814 stores methods, threads, processes, applications, objects, modules, any other sort of executable instruction, or a combination thereof. In some cases, the memory 814 stores files, databases, or a combination thereof. In some examples, the memory 814 includes, but is not limited to, RAM, ROM, electrically erasable programmable read-only memory (EEPROM), flash memory, or any other memory technology. In some examples, the memory 814 includes one or more of CD-ROMs, digital versatile discs (DVDs), content-addressable memory (CAM), or other optical storage, magnetic cassettes, magnetic tape, magnetic disk storage or other magnetic storage devices, or any other medium which can be used to store the desired information and which can be accessed by the processor(s) 812 and/or the external defibrillator 800. In some cases, the memory 814 at least temporarily stores the ECG signal and/or the impedance signal.

In various examples, the memory 814 includes a detector 816, which causes the processor(s) 812 to determine, based on the ECG signal and/or the impedance signal, whether the individual 808 is exhibiting a particular heart rhythm. For instance, the processor(s) 812 determines whether the individual 808 is experiencing a shockable rhythm that is treatable by defibrillation. Examples of shockable rhythms include ventricular fibrillation (VF) and ventricular tachycardia (V-Tach). In some examples, the processor(s) 812 determines whether any of a variety of different rhythms (e.g., asystole, sinus rhythm, atrial fibrillation (AF), etc.) are present in the ECG signal.

The processor(s) 812 is operably connected to one or more input devices 818 and one or more output devices 820. Collectively, the input device(s) 818 and the output device(s) 820 function as an interface between a user and the defibrillator 800. The input device(s) 818 is configured to receive an input from a user and includes at least one of a keypad, a cursor control, a touch-sensitive display, a voice input device (e.g., a speaker), a haptic feedback device, or any combination thereof. The output device(s) 820 includes at least one of a display, a speaker, a haptic output device, a printer, or any combination thereof. In various examples, the processor(s) 812 causes a display among the input device(s) 818 to visually output a waveform of the ECG signal and/or the impedance signal. In some implementations, the input device(s) 818 includes one or more touch sensors, the output device(s) 820 includes a display screen, and the touch sensor(s) are integrated with the display screen. Thus, in some cases, the external defibrillator 800 includes a touchscreen configured to receive user input signal(s) and visually output physiological parameters, such as the ECG signal and/or the impedance signal.

In some examples, the memory 814 includes an advisor 822, which, when executed by the processor(s) 812, causes the processor(s) 812 to generate advice and/or control the output device(s) 820 to output the advice to a user (e.g., a rescuer). In some examples, the processor(s) 812 provides, or causes the output device(s) 820 to provide, an instruction to perform CPR on the individual 808. In some cases, the processor(s) 812 evaluates, based on the ECG signal, the impedance signal, or other physiological parameters, CPR being performed on the individual 808 and causes the output device(s) 820 to provide feedback about the CPR in the instruction. According to some examples, the processor(s) 812, upon identifying that a shockable rhythm is present in the ECG signal, causes the output device(s) 820 to output an instruction and/or recommendation to administer a defibrillation shock to the individual 808.

The memory 814 also includes an initiator 824 which, when executed by the processor(s) 812, causes the processor(s) 812 to control other elements of the external defibrillator 800 in order to administer a defibrillation shock to the individual 808. In some examples, the processor(s) 812 executing the initiator 824 selectively causes the administration of the defibrillation shock based on determining that the individual 808 is exhibiting the shockable rhythm and/or based on an input from a user (received, e.g., by the input device(s) 818. In some cases, the processor(s) 812 causes the defibrillation shock to be output at a particular time, which is determined by the processor(s) 812 based on the ECG signal and/or the impedance signal.

The processor(s) 812 is operably connected to a charging circuit 823 and a discharge circuit 825. In various implementations, the charging circuit 823 includes a power source 826, one or more charging switches 828, and one or more capacitors 830. The power source 826 includes, for instance, a battery. The processor(s) 812 initiates a defibrillation shock by causing the power source 826 to charge at least one capacitor among the capacitor(s) 830. For example, the processor(s) 812 activates at least one of the charging switch(es) 828 in the charging circuit 823 to complete a first circuit connecting the power source 826 and the capacitor to be charged. Then, the processor(s) 812 causes the discharge circuit 825 to discharge energy stored in the charged capacitor across a pair of defibrillation electrodes 830, which are in contact with the individual 808. For example, the processor(s) 812 deactivates the charging switch(es) 828 completing the first circuit between the capacitor(s) 830 and the power source 826, and activates one or more discharge switches 832 completing a second circuit connecting the charged capacitor 830 and at least a portion of the individual 808 disposed between defibrillation electrodes 834.

The energy is discharged from the defibrillation electrodes 834 in the form of a defibrillation shock. For example, the defibrillation electrodes 834 are connected to the skin of the individual 808 and located at positions on different sides of the heart of the individual 808, such that the defibrillation shock is applied across the heart of the individual 808. The defibrillation shock, in various examples, depolarizes a significant number of heart cells in a short amount of time. The defibrillation shock, for example, interrupts the propagation of the shockable rhythm (e.g., VF or V-Tach) through the heart. In some examples, the defibrillation shock is 200 J or greater with a duration of about 0.015 seconds. In some cases, the defibrillation shock has a multiphasic (e.g., biphasic) waveform. The discharge switch(es) 832 are controlled by the processor(s) 812, for example. In various implementations, the defibrillation electrodes 834 are connected to defibrillation leads 836. The defibrillation leads 836 are connected to a defibrillation port 838, in implementations. According to various examples, the defibrillation leads 836 are removable from the defibrillation port 838. For example, the defibrillation leads 836 are plugged into the defibrillation port 838.

In various implementations, the processor(s) 812 is operably connected to one or more transceivers 840 that transmit and/or receive data over one or more communication networks 842. For example, the transceiver(s) 840 includes a network interface card (NIC), a network adapter, a local area network (LAN) adapter, or a physical, virtual, or logical address to connect to the various external devices and/or systems. In various examples, the transceiver(s) 840 includes any sort of wireless transceivers capable of engaging in wireless communication (e.g., radio frequency (RF) communication). For example, the communication network(s) 842 includes one or more wireless networks that include a 3$^{rd}$ Generation Partnership Project (3GPP) network, such as a Long Term Evolution (LTE) radio access network (RAN) (e.g., over one or more LE bands), a New Radio (NR) RAN (e.g., over one or more NR bands), or a combination thereof. In some cases, the transceiver(s) 840 includes other wireless modems, such as a modem for engaging in WI-FI®, WIGIG®, WIMAX®, BLUETOOTH®, or infrared communication over the communication network(s) 842.

The defibrillator 800 is configured to transmit and/or receive data (e.g., ECG data, impedance data, data indicative of one or more detected heart rhythms of the individual 808, data indicative of one or more defibrillation shocks administered to the individual 808, etc.) with one or more external devices 844 via the communication network(s) 842. The external devices 844 include, for instance, mobile devices (e.g., mobile phones, smart watches, etc.), Internet of Things (IoT) devices, medical devices, computers (e.g., laptop devices, servers, etc.), or any other type of computing device configured to communicate over the communication network(s) 842. In some examples, the external device(s) 844 is located remotely from the defibrillator 800, such as at a remote clinical environment (e.g., a hospital). According to various implementations, the processor(s) 812 causes the transceiver(s) 840 to transmit data (e.g., a parameter file) to the external device(s) 844. In some cases, the transceiver(s) 840 receives data from the external device(s) 844 and the transceiver(s) 840 provide the received data to the processor(s) 812 for further analysis. In some implementations, the external device(s) 884 include a recording device and a synchronizer. For example, the synchronizer receives the data from the defibrillator 800 and time-aligns the data with an audio recording detected by the recording device. Although not specifically illustrated in FIG. 8, each one of the external devices 884 includes a processor configured to perform operations and a memory storing instructions for performing the operations.

In various implementations, the external defibrillator 800 also includes a housing 846 that at least partially encloses other elements of the external defibrillator 800. For example, the housing 846 encloses the detection circuit 810, the processor(s) 812, the memory 814, the charging circuit 823, the transceiver(s) 840, or any combination thereof. In some cases, the input device(s) 818 and output device(s) 820 extend from an interior space at least partially surrounded by the housing 846 through a wall of the housing 846. In various examples, the housing 846 acts as a barrier to moisture, electrical interference, and/or dust, thereby protecting various components in the external defibrillator 800 from damage.

In some implementations, the external defibrillator 800 is an automated external defibrillator (AED) operated by an untrained user (e.g., a bystander, layperson, etc.) and can be operated in an automatic mode. In automatic mode, the processor(s) 812 automatically identifies a rhythm in the ECG signal, makes a decision whether to administer a defibrillation shock, charges the capacitor(s) 830, discharges the capacitor(s) 830, or any combination thereof. In some cases, the processor(s) 812 controls the output device(s) 820 to output (e.g., display) a simplified user interface to the untrained user. For example, the processor(s) 812 refrains from causing the output device(s) 820 to display a waveform of the ECG signal and/or the impedance signal to the untrained user, in order to simplify operation of the external defibrillator 800.

In some examples, the external defibrillator 800 is a monitor-defibrillator utilized by a trained user (e.g., a clinician, an emergency responder, etc.) and can be operated in a manual mode or the automatic mode. When the external defibrillator 800 operates in manual mode, the processor(s) 812 cause the output device(s) 820 to display a variety of information that may be relevant to the trained user, such as waveforms indicating the ECG data and/or impedance data, notifications about detected heart rhythms, and the like.

EXAMPLE CLAUSES

1. A system including: a defibrillator including: a sensor configured to detect values of a physiological parameter of a patient in an environment at discrete times in a time interval; a speaker configured to output an audible marker into the environment at a particular time among the discrete times; a first processor configured to generate monitor data including: a parameter channel indicating the physiological parameter at the discrete times; and a marker channel indicating the audible marker output at the particular time; and a first transceiver configured to transmit the monitor data; and a synchronizer including: a second transceiver configured to receive the monitor data from the defibrillator and to receive recorder data from a recording device, the recorder data being indicative of an audio recording of the environment during the time interval; a second processor configured to: detect the audible marker in the audio recording; and generate aligned data by aligning the parameter channel and the audio recording based on the audible marker indicated in the marker channel and detected in the audio recording; and an output device configured to output the aligned data.
2. The system of clause 1, wherein the second processor is further configured to: identify words spoken by a rescuer by performing speech-to-text on an additional sound in the audio recording; and generate a record associated with the patient based on the words.
3. The system of clause 1 or 2, wherein the recording device includes a mobile phone or a wearable device.
4. A synchronizer, including: a receiver configured to: receive monitor data from a medical device, the monitor data indicating a physiological parameter of a patient detected by the medical device during a time interval and a marker output by the medical device into an environment during the time interval; and receive recording data from a recording device, the recording data including an audio recording of the environment during the time interval; a processor; and memory storing instructions that, when executed by the processor, cause the processor to perform operations including: identifying the marker in the audio recording of the environment; and based on identifying the marker in the audio recording of the environment, generating aligned data by time-aligning the physiological parameter of the patient and the audio recording.

5. The synchronizer of clause 4, further including: an output device configured to output the aligned data.
6. The synchronizer of clause 5, wherein the output device includes a screen and a speaker and is configured to output the aligned data by simultaneously: displaying, on the screen, an animation of a waveform of the physiological parameter; and outputting, by the speaker, the audio recording of the environment.
7. The synchronizer of any one of clauses 4 to 6, wherein the operations further include: identifying a voice notation in the audio recording of the environment; determining, based on the aligned data, a discrete time in the time interval when the voice notation occurred; and generating a record associated with the patient, the record indicating the voice notation and the discrete time when the voice notation occurred.
8. The synchronizer of clause 7, wherein identifying the voice notation includes determining that a rescuer has administered a treatment to the patient by performing speech-to-text on the audio recording, and wherein the record further indicates the treatment administered to the patient.
9. The synchronizer of any one of clauses 4 to 8, wherein the marker includes a power up sound of the medical device, a power off sound of the medical device, an audible instruction output by the medical device, or an alarm output by the medical device.
10. The synchronizer of any one of clauses 4 to 9, wherein the medical device includes a defibrillator, an ultrasound device, or a ventilation device.
11. The synchronizer of any one of clauses 4 to 10, wherein the physiological parameter includes an electrocardiogram (ECG), an oxygenation of the patient's blood, an amount of carbon dioxide in the patient's breath, a heart rate of the patient, a blood pressure of the patient, a carboxyhemoglobin level of the patient's blood, a temperature of the patient, a respiration rate of the patient, or a pulse rate of the patient.
12. The synchronizer of any one of clauses 4 to 11, wherein the recorder device includes a mobile device or a wearable device.
13. A method, including: receiving, from a first device, a first file including first measurements of a first parameter at first discrete times in a time interval, the first file further including a marker output by the first device during the time interval; receiving, from a second device, a second file including second measurements of a second parameter at second discrete times in the time interval; detecting the marker output by the first device in the second measurements of the second parameter; based on detecting the signal output by the first device in the second measurements, generating aligned data by time-aligning the first measurements of the first parameter and the second measurements of the second parameter; and outputting the aligned data.
14. The method of clause 13, wherein the first device includes a defibrillator and the second device includes a mobile device or a wearable device.
15. The method of clause 13 or 14, wherein the first parameter includes an electrocardiogram (ECG) of a patient, an oxygenation of the patient's blood, an amount of carbon dioxide in the patient's breath, a heart rate of the patient, a blood pressure of the patient, a carboxyhemoglobin level of the patient's blood, a temperature of the patient, a respiration rate of the patient, or a pulse rate of the patient, and wherein the second parameter includes sound, the second measurements including an audio recording.

16. The method of clause 15, wherein the marker includes a power up sound of the first device, a power off sound of the first device, an audible instruction output by the first device, or an alarm output by the first device.

17. The method of clause 15 or 16, wherein outputting the aligned data includes simultaneously: displaying, on a screen, an animation of a waveform of the first parameter; and outputting, by a speaker, the audio recording.

18. The method of any one of clauses 15 to 17, further including: identifying words by performing speech-to-text on the audio recording; and generating a record including the words and the first measurements of the first parameter.

19. The method of clause 18, further including: determining that a treatment has been administered to a patient based on the words, wherein the record indicates the treatment administered to the patient.

20. The method of clause 18 or 19, further including: transmitting the record to an external computing device.

21. A synchronizer, including: a receiver configured to: receive, from medical devices, parameter files, the parameter files respectively including first channels indicating physiological parameters of patients detected by the medical devices during time intervals and second channels indicating audible markers output by the medical devices during the time intervals; and receive, from recording devices, recording files, the recording files including audio recordings by the recording devices; a processor; and memory storing instructions that, when executed by the processor, cause the processor to perform operations including: selecting a particular parameter file among the parameter files received from a particular medical device among the medical devices, the first channel of the particular medical device indicating a physiological parameter of a particular patient among the patients detected during a particular time interval among the time intervals, the second channel of the parameter file indicating a first audible marker output by the particular medical device in the time interval and a second audible marker output by the medical device in the time interval; identifying a time difference between the first audible marker output by the particular medical device and the second audible marker output by the particular medical device; identifying a set of recording files among the recording files that include audio recordings of the first audible marker and the second audible marker; identifying a particular recording file among the set of recording files indicating the first audible marker and the second audible marker separated by the time difference; and generating aligned data by time-aligning the first channel of the particular parameter file and the particular recording file.

22. The synchronizer of clause 21, wherein the medical devices include defibrillators, and the physiological parameters include electrocardiograms (ECG) of the patients, oxygenations of the patients' blood, amounts of carbon dioxide in the patients' breath, heart rates of the patients, blood pressures of the patients, carboxyhemoglobin levels of the patients' blood, temperatures of the patients, respiration rates of the patients, or pulse rates of the patients.

23. The synchronizer of clause 21 or 22, wherein the recording devices include mobile devices or wearable devices.

24. The synchronizer of any one of clauses 21 to 23, wherein the first audible marker or the second audible marker includes a power up sound of the particular medical device, a power off sound of the particular medical device, an audible instruction output by the particular medical device, or an audible alarm output by the particular medical device.

25. The synchronizer of any one of clauses 21 to 24, further including: an output device configured to output the aligned data.

26. A method including: receiving, from medical devices, parameter files, the parameter files respectively including first channels indicating physiological parameters of patients detected by the medical devices during time intervals and second channels indicating audible markers output by the medical devices during the time intervals; receiving, from recording devices, recording files, the recording files including audio recordings by the recording devices; selecting a particular parameter file among the parameter files received from a particular medical device among the medical devices, the first channel of the particular medical device indicating a physiological parameter of a particular patient among the patients detected during a particular time interval among the time intervals, the second channel of the parameter file indicating a first audible marker output by the particular medical device in the time interval and a second audible marker output by the medical device in the time interval; identifying a time difference between the first audible marker output by the particular medical device and the second audible marker output by the particular medical device; identifying a set of recording files among the recording files that include audio recordings of the first audible marker and the second audible marker; identifying a particular recording file among the set of recording files indicating the first audible marker and the second audible marker separated by the time difference; and generating aligned data by time-aligning the first channel of the particular parameter file and the particular recording file.

27. The method of clause 26, wherein the medical devices include defibrillators, and the physiological parameters include electrocardiograms (ECG) of the patients, oxygenations of the patients' blood, amounts of carbon dioxide in the patients' breath, heart rates of the patients, blood pressures of the patients, carboxyhemoglobin levels of the patients' blood, temperatures of the patients, respiration rates of the patients, or pulse rates of the patients.

28. The method of clause 26 or 27, wherein the recording devices include mobile devices or wearable devices.

29. The method of any one of clauses 26 to 28, wherein the first audible marker or the second audible marker includes a power up sound of the particular medical device, a power off sound of the particular medical device, an audible instruction output by the particular medical device, or an audible alarm output by the particular medical device.

30. The method one of clauses 26 to 29, further including: outputting the aligned data.

31. The method of one of clauses 26 to 30, further including: identifying words in the particular recording file; generating a record associated with the particular patient based on the words; and transmitting the record to an external computing device.

32. The method of clause 31, further including: determining that the words in the particular recording file indicate a treatment administered to the patient during the time interval, wherein the record further indicates the treatment administered to the patient during the time interval.

33. A system including: a medical device including: a receiver configured to receive timing signals from satellites; a sensor configured to detect values of a physiological parameter of a patient at discrete times during a time interval; a processor configured to: identify the discrete times based on the timing signals; and generate a parameter file including a first channel and a second channel, the first channel including the physiological parameter of the patient and the second channel including the discrete times; and a synchronizer including: a receiver configured to: receive the parameter file from the medical device; receive, from a recording device, a recording file including a third channel indicating an audio recording detected by the recording device during the time interval and a fourth channel indicating the discrete times; a processor; and memory storing instructions that, when executed by the processor, cause the processor to perform operations including: generating aligned data by time-aligning the first channel and the third channel based on the discrete times indicated in the second channel and the fourth channel; and an output device configured to output the aligned data.

34. The system of clause 33, wherein the output device includes a screen and a speaker and is configured to output the aligned data by simultaneously: displaying, on the screen, an animation of a waveform of the physiological parameter; and outputting, by the speaker, the audio recording.

35. The system of clause 33 or 34, wherein the operations further include: identifying a voice notation in the audio recording; determining, based on the aligned data, a discrete time in the time interval when the voice notation occurred; and generating a record associated with the patient, the record indicating the voice notation and the discrete time when the voice notation occurred.

36. The system of clause 35, wherein identifying the voice notation includes determining that a rescuer has administered a treatment to the patient by performing speech-to-text on the audio recording, and wherein the record further indicates the treatment administered to the patient.

37. The system of any one of clauses 33 to 36, wherein the medical device includes a defibrillator.

38. The system of any one of clauses 33 to 37, wherein the physiological parameter includes an electrocardiogram (ECG), an oxygenation of the patient's blood, an amount of carbon dioxide in the patient's breath, a heart rate of the patient, a blood pressure of the patient, a carboxyhemoglobin level of the patient's blood, a temperature of the patient, a respiration rate of the patient, or a pulse rate of the patient.

39. The system of any one of clauses 33 to 38, wherein the recorder device includes a mobile device or a wearable device.

40. A method, including: identifying a first file including first measurements of a first parameter at first discrete times in a time interval, the first file further including a marker output by the first device during the time interval; identifying a second file including second measurements of a second parameter at second discrete times in the time interval; detecting the marker output by the first device in the second measurements of the second parameter; and based on detecting the signal output by the first device in the second measurements, generating aligned data by time-aligning the first measurements of the first parameter and the second measurements of the second parameter.

41. The method of clause 40, wherein the first file and the second file are generated by different devices.

42. The method of clause 40 or 41, wherein the operations further include: outputting the aligned data.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing implementations of the disclosure in diverse forms thereof.

As will be understood by one of ordinary skill in the art, each implementation disclosed herein can comprise, consist essentially of or consist of its particular stated element, step, or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the implementation to the specified elements, steps, ingredients or components and to those that do not materially affect the implementation. As used herein, the term "based on" is equivalent to "based at least partly on," unless otherwise specified. The term "being indicative of" may refer to something that indicates or otherwise shows another feature.

Unless otherwise indicated, all numbers expressing quantities, properties, conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing implementations (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate implementations of the disclosure and does not pose a limitation on the scope of the disclosure. No language in the specification should be construed as indicating any non-claimed element essential to the practice of implementations of the disclosure.

Groupings of alternative elements or implementations disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain implementations are described herein, including the best mode known to the inventors for carrying out implementations of the disclosure. Of course, variations on these described implementations will become apparent to those of ordinary skill in the art upon reading the foregoing description. The inventor expects skilled artisans to employ such variations as appropriate, and the inventors intend for implementations to be practiced otherwise than specifically described herein. Accordingly, the scope of this disclosure includes all modifications and equivalents of the subject matter recited in the claims appended hereto as permitted by applicable law. Moreover, any combination of the above-described elements in all possible variations thereof is encompassed by implementations of the disclosure unless otherwise indicated herein or otherwise clearly contradicted by context.

What is claimed is:

1. A system comprising:
a defibrillator comprising:
a sensor configured to detect values of a physiological parameter of a patient in an environment at discrete times in a time interval;
a speaker configured to output an audible marker into the environment at a particular time among the discrete times;
a first processor configured to generate monitor data comprising:
a parameter channel indicating the values of the physiological parameter at the discrete times; and a marker channel indicating the audible marker output at the particular time; and
a first transceiver configured to transmit the monitor data; and
a synchronizer comprising:
a second transceiver configured to receive the monitor data from the defibrillator and to receive recorder data from a recording device that is separate from the defibrillator, the recorder data being indicative of an audio recording of the environment during the time interval;
a second processor configured to:
detect the audible marker in the audio recording; and
generate aligned data by aligning the parameter channel and the audio recording based on the audible marker indicated in the marker channel and detected in the audio recording; and
an output device configured to output the aligned data.

2. The system of claim 1, wherein the second processor is further configured to:
identify words spoken by a rescuer by performing speech-to-text on an additional sound in the audio recording; and
generate a record associated with the patient based on the words.

3. The system of claim 1, wherein the recording device comprises a mobile phone or a wearable device.

4. A synchronizer, comprising:
a receiver configured to:
receive monitor data from a medical device, the monitor data comprising:
a first channel indicating values of a physiological parameter of a patient detected by the medical device during a time interval; and
a second channel indicating a marker output by the medical device into an environment during the time interval; and
receive recording data from a recording device that is separate from the medical device, the recording data comprising:
a third channel comprising an audio recording of the environment during the time interval;
a processor; and
memory storing instructions that, when executed by the processor, cause the processor to perform operations comprising:
identifying the marker in the third channel comprising the audio recording of the environment; and
based on identifying the marker in the third channel comprising the audio recording of the environment, generating aligned data comprising:
the first channel; and
the third channel time-aligned with the first channel.

5. The synchronizer of claim 4, further comprising:
an output device configured to output the aligned data, the output device comprising a screen and a speaker,
wherein the output device is configured to output the aligned data by simultaneously:
displaying, on the screen, an animation of a waveform of the physiological parameter; and
outputting, by the speaker, the audio recording of the environment.

6. The synchronizer of claim 4, wherein the operations further comprise:
identifying a voice notation in the audio recording of the environment;

determining, based on the aligned data, a discrete time in the time interval when the voice notation occurred; and generating a record associated with the patient, the record indicating the voice notation and the discrete time when the voice notation occurred.

7. The synchronizer of claim 6, wherein identifying the voice notation comprises determining that a rescuer has administered a treatment to the patient by performing speech-to-text on the audio recording, and wherein the record further indicates the treatment administered to the patient.

8. The synchronizer of claim 4, wherein the marker comprises a power up sound of the medical device, a power off sound of the medical device, an audible instruction output by the medical device, or an alarm output by the medical device.

9. The synchronizer of claim 4, wherein the medical device comprises a defibrillator, and wherein the recording device comprises a mobile device or a wearable device.

10. The synchronizer of claim 4, wherein the physiological parameter comprises an electrocardiogram (ECG), an oxygenation of the patient's blood, an amount of carbon dioxide in the patient's breath, a heart rate of the patient, a blood pressure of the patient, a carboxyhemoglobin level of the patient's blood, a temperature of the patient, a respiration rate of the patient, or a pulse rate of the patient.

11. The synchronizer of claim 4, wherein the medical device and the recording device have different internal clocks.

12. The synchronizer of claim 4, wherein the first channel of the monitor data indicates the values of the physiological parameter at a first sampling rate, wherein the third channel of the recording data indicates the audio recording of the environment at a second sampling rate, and wherein the first sampling rate is different than the second sampling rate.

13. The synchronizer of claim 4, wherein the monitor data further comprises a fourth channel comprising first timestamps, wherein the recording data further comprises a fifth channel comprising second timestamps, and wherein the first timestamps are different than the second timestamps.

14. A method, comprising:

receiving, from a first device, a first file comprising:

a first channel comprising first measurements of a first parameter at first discrete times in a time interval; and a second channel comprising an indication of a marker output by the first device during the time interval;

receiving, from a second device that is separate from the first device, a second file comprising a third channel that comprises second measurements of a second parameter at second discrete times in the time interval;

detecting, by analyzing the third channel, the marker output by the first device in the second measurements of the second parameter;

based on detecting the marker output by the first device in the second measurements, generating aligned data comprising the first channel time-aligned with the third channel; and outputting the aligned data.

15. The method of claim 14, wherein the first device comprises a defibrillator and the second device comprises a mobile device or a wearable device.

16. The method of claim 14, wherein the first parameter comprises an electrocardiogram (ECG) of a patient, an oxygenation of the patient's blood, an amount of carbon dioxide in the patient's breath, a heart rate of the patient, a blood pressure of the patient, a carboxyhemoglobin level of the patient's blood, a temperature of the patient, a respiration rate of the patient, or a pulse rate of the patient, and wherein the second parameter comprises sound, the second measurements comprising an audio recording.

17. The method of claim 16, wherein the marker comprises a power up sound of the first device, a power off sound of the first device, an audible instruction output by the first device, or an alarm output by the first device.

18. The method of claim 14, wherein outputting the aligned data comprises simultaneously:

displaying, on a screen, an animation of a waveform of the first parameter; and outputting, by a speaker, an audio recording indicating the second measurements of the second parameter.

19. The method of claim 16, further comprising:

identifying words by performing speech-to-text on the audio recording;

generating a record comprising the words and the first measurements of the first parameter; and transmitting the record to an external computing device.

20. The method of claim 19, further comprising:

determining that a treatment has been administered to a patient based on the words, wherein the record indicates the treatment administered to the patient.

* * * * *